United States Patent [19]

Silkoff et al.

[11] Patent Number: 5,795,787
[45] Date of Patent: Aug. 18, 1998

[54] METHOD AND APPARATUS FOR THE MEASUREMENT OF EXHALED NITRIC OXIDE IN HUMANS

[76] Inventors: Philip Silkoff, Apt. 610, 640 Roselawn Ave., Toronto, Ontario, Canada, M5N 1K9; Patricia McClean, 200 Elizabeth St., Toronto, Ontario, Canada, M5G 2C4

[21] Appl. No.: 629,594

[22] Filed: Apr. 9, 1996

[51] Int. Cl.$^6$ .................................................. G01N 33/00
[52] U.S. Cl. .......................... 436/116; 436/106; 422/83; 422/84; 128/201.18; 128/203.14; 128/204.22; 128/206.29
[58] Field of Search .................... 436/106, 116, 436/118, 900; 128/201.18, 203.12, 203.14, 204.22, 206.15, 206.29; 422/83–84

[56] References Cited

U.S. PATENT DOCUMENTS

| | | | |
|---|---|---|---|
| 3,726,270 | 4/1973 | Griffis et al. | 128/2.08 |
| 3,785,370 | 1/1974 | Richards et al. | |
| 3,951,607 | 4/1976 | Fraser | |
| 4,083,367 | 4/1978 | Portner et al. | |
| 4,090,078 | 5/1978 | Heim | 280/343 |
| 4,202,352 | 5/1980 | Osborn | |
| 4,735,777 | 4/1988 | Mitsui et al. | |
| 4,772,559 | 9/1988 | Preti et al. | |
| 4,796,639 | 1/1989 | Snow et al. | |
| 5,042,501 | 8/1991 | Kenney et al. | |
| 5,081,871 | 1/1992 | Glaser | |
| 5,447,165 | 9/1995 | Gustafsson | |
| 5,531,218 | 7/1996 | Krebs | 128/203.12 |

FOREIGN PATENT DOCUMENTS

| | | |
|---|---|---|
| 0573060 | 12/1993 | European Pat. Off. |
| 0650051 | 4/1995 | European Pat. Off. |
| 3844455 | 8/1989 | Germany |
| 95/02181 | 1/1995 | WIPO |

OTHER PUBLICATIONS

Brooks, Lee J. et al., "Reproducibility and accuracy of airway area by acoustic reflection;" J. Appl. Physiol.: Respirat. Enriron. Exercise Physiol 57(3): 77–787, 1984.

Fredberg, Jeffrey J. et al., "Airway area by acoustic reflections measured at the mouth:" J. Appl. Physiol.: Respirat. Environ. Exercise Physiol. 48(5):749–758, 1980.

Rubinstein, I. et al., "Effect of mouthpiece, noseclips, and head position on airway area measured by acoustic reflections;" J. Appl. Physiol. 63(4):1469–1474, 1987.

Saidel, G. et al., "The Respiratory System: Analysis of Function and Applications;" A Special Issue of Annals of Biomedical Engineering, Pergamon Press, New York.

Sidell, R. et al., Noninvasive Inference of Airway Network Geometry From Broadband Lung Reflection Data; Journal of Biomechanical Engineering, vol. 100, pp. 131–138, 1978.

Husain et al., "Exhaled Nitric Oxide as a marker for Organic Nitrate Tolerance", Circulation, vol. 89, No. 6, Jun. 1994, #2498 on p. A 19.

Gustafsson et al., "Endogenous Nirtric Oxide is Present in the Exhaled Air . . . And Humans", Biochem Biophys Res Com, vol. 181, No. 2, pp. 852–857, Dec. 16, 1991.

Anggard, E.; "Nitric Oxide: mediator, murderer, and medicine; review article"; The Lancet; May 1994; vol. 343; No. 8907, p. 1199.

Borland, CDR., et al.; "A simultaneous single breath measurement of pulmonary diffusing capacity with nitric oxide and carbon monoxide"; Eur Respir J; 1989, 2, pp. 56–63.

Brett, S.J. et al.; "Endogenous Nitric Oxide in Exhaled Human Breath"; Chest;110.4.Oct. 1996, p. 873.

(List continued on next page.)

*Primary Examiner*—Lyle A. Alexander
*Attorney, Agent, or Firm*—Morgan, Lewis & Bockius LLP

[57] ABSTRACT

An apparatus for measuring nitric oxide exhaled from the lungs of a person comprises (a) a conduit for receiving the air exhaled by the person;

(b) a resistor for increasing the pressure in the mouth of the person during exhalation to close the nasopharynx and to maintain a constant flow rate of said air exhaled by the person; and, (c) measuring means for measuring the nitric oxide concentration in said exhaled air.

11 Claims, 1 Drawing Sheet

OTHER PUBLICATIONS

Fallat, R. et al.; "Distribution of Ventillation"; in Wilson, A.F., Editor, Pulmonary Function Testing Indications and Interpretations; Pulmonary Function Testing Indications and Interpretations; Grune & Stratton, Inc. (1985).

Guenard, H. et al.; "Determination of lung capilary blood volume and membrane diffusing capacity in man . . . "; Respiration Physiology (1987) 70, pp. 133–120.

Hills, E.A. et al.; "Membrane diffusing capacity and pulmonary capillary volume in rheumatoid disease"; Thorax 1980 Nov.; 35(11); pp. 851–855.

Kharitonov, S.A. et al.; "Increased nitric oxide in exhaled air of asthmatic patients"; The Lancet; vol. 343 (Jan. 15, 1994), pp. 133–135.

Kilbourn, R.G., et al.; "Endothelial Cell Production of Nitrogen Oxides in Response to Interferon . . ."; HHS; NCI. J Natl Cancer Inst., May 2, 1990; pp. 32–38.

Leone, A.M. et al.; "Nitric Oxide is Present in Exhaled Breath in Humans . . . "; Biochemical and Biophysical Research Communications; vol. 201, No. 2, 1994, pp. 883–887.

Lundberg, Jon, "Airborne Nitric Oxide: Inflammatory Marker . . . "; ACTA Physiologica Scandinavica Supplementum 633; Stockholm 1996; pp. 1–27.

Manicatide M.A. et al.; "Breathlessness and transfer factor for the lung . . . "; Rev. Roum Med Intern 1975; 13(1); pp. 53–57 (Abstract Only).

Meyer, M. et al.; "Nitric oxide (NO), a new test gas . . . "; Eur Respir J., 1989, vol. 2, pp. 494–496.

Moinard, J. et al.; "Determination of lung capillary blood volume and membrane diffusing capacity . . . "; Eur Respir J; 1990, 3, pp. 318–322.

Moncada, S.; "Nitric Oxide"; Journal of Hypertension; 1994, 12 (Suppl. 10); pp. S35–S39.

Morrison, D. et al.; "Reduced Exercise Capacity of Chronic Obstructive Pulmonary . . . "; The American Journal of Cardiology; vol. 64; pp. 1180–1184.

Nathan, Carl F., et al.; "Does Endothelium–Derived Nitric Oxide Have a Role in Cytokine–Induced Hypotension?"; Journal of National Cancer Institute; May 2, 1990, 82: pp. 726–728.

Persson; Magnus G. et al.; "Single–breath nitric oxide measurements in asthmatic patients and smokers"; The Lancet; vol. 343 (Jan. 15, 1994).

Persson; M.G. et al.; "Endogenous nitric oxide as a probable modulator . . . "; Acta Physiol Scand 1990, 140; pp. 449–457.

Scheideler, L., et al.; "Detection of Nonvolatile Macromolecules . . . "; Am Rev Respir Dis., vol. 148; 1993; pp. 778–784.

Sherman, M.P. et al.; "Cytokine–and Pneumocystic carinii–induced L–arginine oxidation . . . " J. Protozool 1991 Nov.–Dec.; 38 (6); pp. 234S–236S (Abstract Only).

Silkoff, P.E. et al., "Marked Flow–dependence of Exhaled Nitric Oxide . . . ", American Journal of Respiratory and Critical Care Medicine; vol. 155; 1997, pp. 260–267.

Swenson, E. et al.; "Conducting airway gas exchange: diffusion–related differences in inert gas elimination"; Airway Gas Exchange; pp. 1581–1588.

Vane, John R. et al.; "Mechanisms of Disease, Regulatory Functions . . . "; New England Journal of Medicine; Jul. 5, 1990; 323: pp. 27–36.

Yoshida, K. et al.; "Biotransformation of Nitric Oxide, Nitrite and Nitrate"; Int. Arch Occup Environ Health (1983) 52:103–115.

Yoshida, K. et al.; "Biotransformation of Nitric Oxide"; Environmental Health Perspectives; vol. 73, pp. 201–206 (1987).

1

METHOD AND APPARATUS FOR THE MEASUREMENT OF EXHALED NITRIC OXIDE IN HUMANS

FIELD OF THE INVENTION

This invention relates to the measurement of nitric oxide in air exhaled by people.

BACKGROUND TO THE INVENTION

Exhaled nitric oxide (NO) can be measured in people and shows promise as a diagnostic tool in airway diseases and in particular bronchial asthma. Asthmatic patients have very high exhaled NO levels as compared to normal subjects and these levels decrease rapidly after the institution of anti-inflammatory therapy. Thus exhaled NO in conjunction with existing tests may aid in the diagnosis and assessment of asthma, and also be an index of the response to therapy, or patient compliance with therapy. In view of the importance of asthma as a major health problem, the commercial potential of a test that can help with the diagnosis, assess severity and ascertain the response to therapy is great.

The measurement method is eminently suitable for the outpatient setting. The test is quick and easy to perform by medical staff and comfortable for the patient so that a pulmonary NO measurement system could become a routine part of the lung function assessment in every respirology clinic.

Published methods to date suffer from two problems. Firstly, in order to measure NO which originates from the lower respiratory tract only, nitric oxide emerging from the nasal cavity which enters the airstream via the nasopharynx and then emerges through the mouth should be excluded. Secondly, exhaled NO concentrations are altered greatly by the expiratory flow rate.

SUMMARY OF THE INVENTION

Pursuant to this invention, positive mouth pressure is used to close the vellum, thus excluding entrainment of nasal NO. Secondly one or more low standardised flow rates, (eg. 10–20 ml/s) is used by introducing fixed expiratory resistances into the expiratory limb of the test circuit. These flow rates amplify the NO signal allowing greater differentiation between health and disease while also permitting direct intersubject of post-therapeutic comparisons. It is possible however to measure at any flow rate by varying the pressure/flow characteristics of the breathing circuit.

According to one embodiment of this invention, an apparatus for measuring nitric oxide exhaled from the lungs of a person comprises conduit means for receiving the air exhaled by the person, means for increasing the pressure in the mouth of the person during exhalation to close the nasopharynx and to maintain a constant flow rate of said air exhaled by the person, and measuring means for measuring the nitric oxide concentration in said exhaled air.

The means may comprise resistance means in said conduit for reducing the flow rate of said air exhaled by the person through said conduit means and pressure measurement means for assisting the person to maintain said air exhaled by the person at a constant pressure. The pressure measurement means may include means for instantaneously displaying the pressure in said conduit wherein the person adjusts the force of the exhalation to maintain a constant pressure in said conduit.

According to another embodiment of this invention, a method of measuring nitric oxide exhaled from the lungs of a person comprising, during exhalation, increasing the pressure in the mouth of the person to close the nasopharynx and to maintain a constant flow rate of said air exhaled by the person; and, measuring the nitric oxide concentration in said exhaled air.

DESCRIPTION OF THE DRAWING

This and other advantages of the present invention will be more fully and completely understood by reference to the following description of the following drawing of an exemplary embodiment of the invention in which.

DESCRIPTION OF PREFERRED EMBODIMENT

Figure 1:
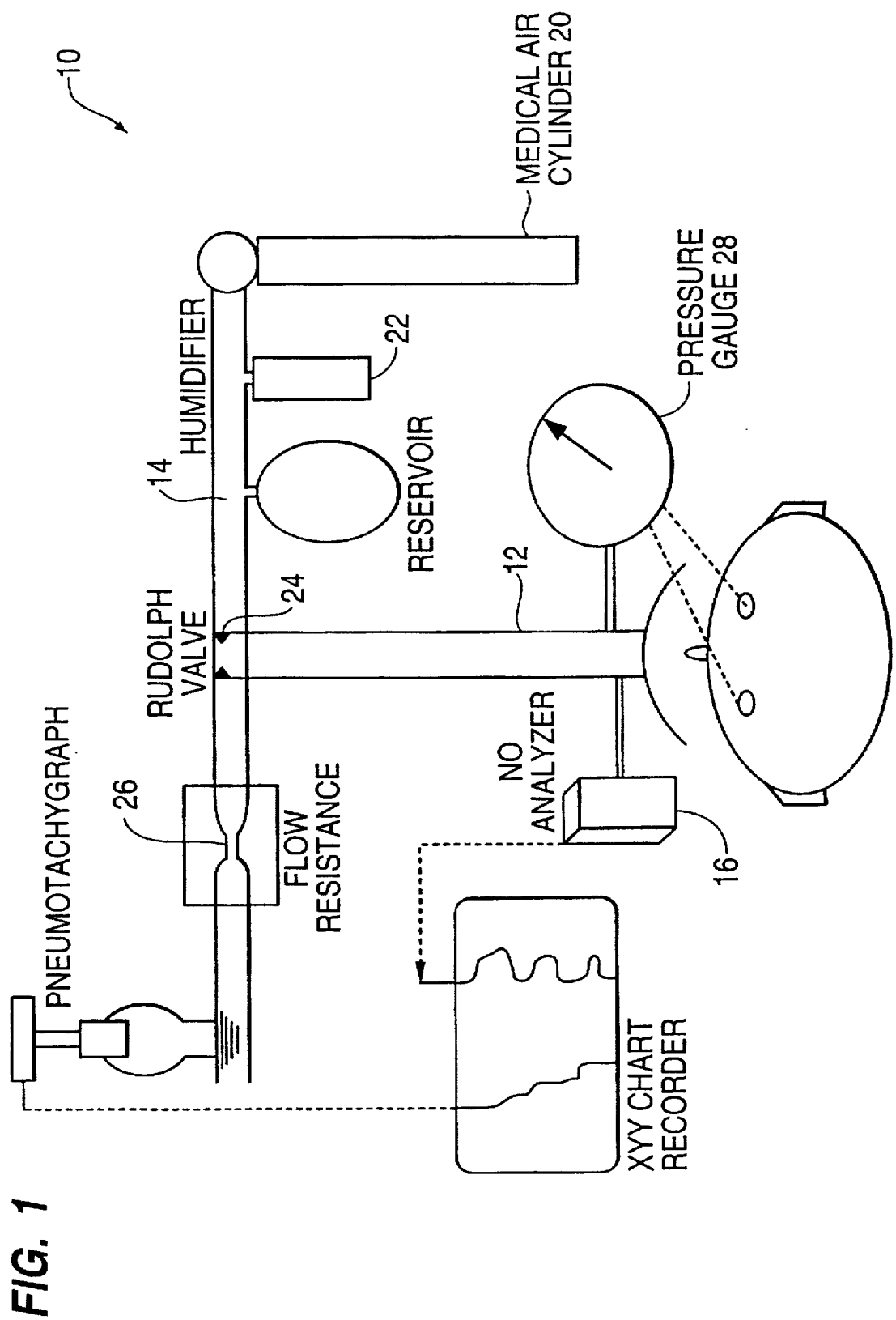
FIG. 1 is a schematic diagram of an apparatus according to the instant invention.

As shown in FIG. 1, apparatus 10 comprises conduit means 12, air supply conduit means 14 and NO analyzer means 16.

Pursuant to the preferred embodiment, air having a defined concentration is supplied through a cylinder 20. By using air of a defined quality, the NO measurement obtained from the exhaled air may be normalized to take into account any NO which may be present in the feed air.

The air may be treated by a humidifier 22. Subsequently, the air travels through conduit 14 and conduit 12 for inhalation by the patient. The patient subsequently exhales into conduit 12. The air travels through conduit 12, past Rudolph valve 24 and subsequently through constriction 26 in the conduit. Constriction 26 causes an increase in pressure in conduit 12 and, accordingly, an increase in pressure is sufficient to close, or at least substantially close, the vellum.

As the person exhales, the air may be sampled by NO analyzer means 16 to measure the level of NO in the exhaled air. Pressure gauge 28 is in flow communication with conduit 12 and preferably provides effectively an instantaneous measure of the pressure in conduit 12. On exhalation, the patient monitors the pressure in conduit 12 and adjusts their exhalation to maintain the pressure, preferably, at the same level or, at least substantially at the same level.

EXAMPLE

Apparatus 10 may be used in conjunction with any commercially available rapid response NO analyzer eg. the Sievers 270B (Boulder, Colo.) rapid chemiluminescent analyzer.

The single breath profile of exhaled nitric oxide (eNo) (with nose clip) has been reported as an early NO peak (NOp) followed by a NO plateau (NOpl) which may correspond to lung NO. Recent evidence suggests that nasal nitric oxide (nNO) is high and gives rise to NOp.

NOpl was measured with a Sievers 270B analyzer. The measurement circuit consisted of a mouthpiece connected to a two-way non-rebreathing valve, through which the seated patient inhales humidified "medical air" (21% oxygen, balance nitrogen) form a reservoir. No nose clip was used. 10 healthy subjects inserted the mouthpiece, inhaled immediately to total lung capacity (TLC) and immediately exhale. During the expiration, the subjects maintained a constant mouth pressure of 20 mm Hg displayed to them on the dial of a pressure gauge to close the vellum thus excluding nNO (confirmed by nasal $CO_2$ probe). 9 separate flows were examined Nopl for (4.2 to 1550 ml/s) using variable expiratory resistances.

NOp was absent with the 20 mm Hg mouth pressure. Ln(NOpl) fell linearly as Ln(expiratory flow) rose (Nopl=e ($5^{1727-0.5132(Ln(flow\ rate))}$, $R^2=0.808$) with a more than 20-fold variation in mean NOpl (5.1±1.4 ppb to 112.5±54.89 ppb) as expiratory flow (EF) varied from 4.2 to 1550 ml/s. Ln NO excretion (NOpl×EF) however rose linearly with Ln EF. A 30s breathold produced the highest values of NOpl for all subjects (178.1±100.8 ppb). Nopl was reduced at FRC as compared to TLC (about −20%, p=0.009) but was not affected by the level of expiratory pressure employed (20 mm Vs 60 mm Hg, p=0.09).

We claim:

1. An apparatus for measuring nitric oxide exhaled from the lungs of a person comprising:
   (a) conduit means for receiving the air exhaled by the person;
   (b) means for introducing resistance in said conduit means for increasing the pressure in the mouth of the person during exhalation to substantially close the vellum and exclude nitric oxide emerging from the nasal cavity and to maintain a constant flow rate of said air exhaled by the person; and,
   (c) measuring means for measuring the nitric oxide concentration in said exhaled air.

2. The apparatus as claimed in claim 1 wherein said means comprises resistance means in said conduit for reducing the flow rate of said air exhaled by the person through said conduit means and pressure measurement means for assisting the person to maintain said air exhaled by the person at a substantially constant pressure.

3. The apparatus as claimed in claim 1 wherein said pressure measurement means includes means for instantaneously displaying the pressure in said conduit such that the person may adjust the force of the exhalation to maintain a substantially constant pressure in said conduit.

4. A method of measuring nitric oxide exhaled from the lungs of a person into a test circuit comprising, during exhalation, increasing the pressure in the mouth of the person by introducing resistance into the test circuit sufficient to substantially close the nasopharynx and to maintain a constant flow rate of said air exhaled by the person; and, measuring the nitric oxide concentration in said exhaled air.

5. The method of claim 4, wherein said constant flow rate falls within the range of 4.2 to 1550 ml/s.

6. The method of claim 5, wherein said constant flow rate falls within the range of 10–20 ml/s.

7. A method for measuring nitric oxide exhaled by a subject, comprising the steps of:
   causing the subject to exhale by mouth into an apparatus for receiving exhaled air;
   wherein said apparatus comprises means to increase the pressure in the mouth of the subject to a level sufficient to cause the vellum of the subject to substantially close and thereby exclude nitric oxide of nasal origin that otherwise would enter the air stream via the nasopharynx during exhalation; and
   measuring the level of nitric oxide of the collected exhaled breath.

8. The method of claim 7, wherein said measured nitric oxide substantially originates from the lower respiratory tract.

9. The method of claim 8, further comprising the step of maintaining a constant flow rate of the exhaled breath of the subject.

10. The method of claim 9, wherein said constant flow rate is accomplished by a resistance means associated with or in flow connection with said receiving apparatus.

11. The method of claim 10, wherein said maintaining a constant flow rate is effected by providing the subject with an instantaneous display of the pressure of the exhaled breath and the subject adjusts the force of the exhalation to maintain a substantially constant pressure.

* * * * *